United States Patent
Vetter

(10) Patent No.: US 11,129,600 B2
(45) Date of Patent: Sep. 28, 2021

(54) DEVICES AND METHODS FOR SOFT TISSUE BIOPSY AND TISSUE SAMPLE COLLECTION

(71) Applicant: TransMed7, LLC, Portola Valley, CA (US)

(72) Inventor: James W Vetter, Portola Valley, CA (US)

(73) Assignee: TransMed7 LLC, Portola Valley, CA (US)

( * ) Notice: Subject to any disclaimer, the term of this patent is extended or adjusted under 35 U.S.C. 154(b) by 356 days.

(21) Appl. No.: 15/990,774

(22) Filed: May 28, 2018

(65) Prior Publication Data

US 2020/0000445 A1 Jan. 2, 2020

(51) Int. Cl.
*A61B 10/02* (2006.01)
*A61B 17/32* (2006.01)
*A61B 17/3205* (2006.01)

(52) U.S. Cl.
CPC .... *A61B 10/0275* (2013.01); *A61B 17/32002* (2013.01); *A61B 10/0266* (2013.01); *A61B 17/32053* (2013.01); *A61B 2010/0225* (2013.01); *A61B 2017/320032* (2013.01)

(58) Field of Classification Search
CPC .... A61B 10/0275; A61B 2017/320032; A61B 10/0266; A61B 17/320758
See application file for complete search history.

(56) References Cited

U.S. PATENT DOCUMENTS

| | | | | |
|---|---|---|---|---|
| 4,660,267 A | * | 4/1987 | Wheeler | A61B 17/32002 29/437 |
| 5,630,826 A | * | 5/1997 | Sastri | A61B 17/32002 606/170 |
| 6,063,037 A | * | 5/2000 | Mittermeier | A61B 10/025 600/567 |
| 8,808,186 B2 | | 8/2014 | Fruland et al. | |
| 9,492,192 B2 | | 11/2016 | To et al. | |
| 2001/0014805 A1 | | 8/2001 | Burbank et al. | |
| 2003/0216759 A1 | | 11/2003 | Burbank et al. | |
| 2004/0077938 A1 | * | 4/2004 | Mark | A61B 17/3403 600/411 |
| 2005/0027210 A1 | * | 2/2005 | Miller | A61B 10/0275 600/567 |
| 2005/0101983 A1 | | 5/2005 | Loshakove et al. | |
| 2007/0073326 A1 | * | 3/2007 | Miller | A61B 10/0275 606/180 |
| 2008/0004643 A1 | | 1/2008 | To et al. | |

(Continued)

*Primary Examiner* — Sean P Dougherty
(74) *Attorney, Agent, or Firm* — Young Law Firm, P.C.

(57) ABSTRACT

A device comprises an outer tube defining a longitudinal axis and comprising an aperture near a distal end thereof; a cutting element disposed within the outer tube and configured for rotation and movement across the aperture along the longitudinal axis, the cutting element comprising an engagement feature at a distal end thereof; and a distal tip comprising a tapered distal end and a proximal end that comprises a mating feature. The cutting element may be configured to rotate and cut tissue as it moves along the longitudinal axis across the aperture until the engagement feature at least partially engages the mating feature of the proximal end of the distal tip and entrains the distal tip in oscillation along the longitudinal axis and/or rotation.

14 Claims, 5 Drawing Sheets

(56) References Cited

U.S. PATENT DOCUMENTS

| | | | |
|---|---|---|---|
| 2009/0270812 A1* | 10/2009 | Litscher | A61M 1/0082 604/164.01 |
| 2010/0030104 A1* | 2/2010 | Hardin | A61B 10/0275 600/566 |
| 2010/0049225 A1 | 2/2010 | To et al. | |
| 2010/0063415 A1* | 3/2010 | Ritchart | A61B 6/12 600/567 |
| 2010/0125253 A1 | 5/2010 | Olson et al. | |
| 2010/0152756 A1* | 6/2010 | Mark | A61B 17/32002 606/167 |
| 2010/0152758 A1* | 6/2010 | Mark | A61B 10/0275 606/171 |
| 2010/0152762 A1* | 6/2010 | Mark | A61B 17/3421 606/180 |
| 2011/0208222 A1* | 8/2011 | Ljahnicky | A61B 17/320758 606/159 |
| 2011/0306995 A1 | 12/2011 | Moberg | |
| 2012/0150066 A1* | 6/2012 | Goldenberg | A61B 10/0275 600/562 |
| 2012/0245487 A1* | 9/2012 | Eells | A61B 10/0275 600/567 |
| 2013/0090674 A1 | 4/2013 | Escudero et al. | |
| 2013/0096459 A1* | 4/2013 | Vetter | A61B 10/0266 600/567 |
| 2014/0180135 A1 | 6/2014 | Hoseit et al. | |
| 2014/0222044 A1 | 8/2014 | Ladd et al. | |
| 2014/0222045 A1 | 8/2014 | Schneider et al. | |
| 2015/0057566 A1* | 2/2015 | Vetter | A61B 10/0266 600/566 |
| 2015/0209066 A1 | 7/2015 | Dahm et al. | |
| 2015/0238224 A1 | 8/2015 | Simpson et al. | |
| 2015/0327884 A1 | 11/2015 | Moberg | |
| 2016/0029902 A1 | 2/2016 | Smith et al. | |
| 2018/0021055 A1 | 1/2018 | Simpson et al. | |
| 2018/0256039 A1 | 9/2018 | Smith et al. | |
| 2018/0368688 A9 | 12/2018 | Simpson et al. | |
| 2019/0303343 A1* | 10/2019 | Vetter | A61B 10/0266 |

\* cited by examiner

DEVICES AND METHODS FOR SOFT TISSUE BIOPSY AND TISSUE SAMPLE COLLECTION

BACKGROUND

Embodiments relate to medical devices and methods. More particularly, embodiments relate to single or multiple insertion, single or multiple sample biopsy medical devices.

SUMMARY

Embodiments are drawn to medical devices and methods that are used for single insertion, single sample and single insertion, multiple sample biopsies, including advanced features for vascular interventional devices used for crossing chronic total vascular occlusions and de-bulking. One embodiment is a tissue biopsy device that comprises a tubular penetration, coring and part-off assembly that minimizes resistance through tissues during one or all of these functions. Embodiments may comprise structures and functionality for tissue penetration, coring, capturing, parting off and retrieving tissue samples from a target biopsy site for subsequent pathological analysis. Embodiments may be portable, disposable or reusable and may be mechanically, manually or electrically powered and operated.

One embodiment, therefore, may comprise a device comprising an outer tube defining a longitudinal axis and comprising an aperture near a distal end thereof; a cutting element disposed within the outer tube and configured for rotation and movement across the aperture along the longitudinal axis, the cutting element comprising an engagement feature at a distal end thereof; and a distal tip comprising a tapered distal end and a proximal end that comprises a mating feature. The cutting element may be configured to rotate and cut tissue as it moves along the longitudinal axis across the aperture until the engagement feature at least partially engages the mating feature of the proximal end of the distal tip and entrains the distal tip in at least one of oscillation along the longitudinal axis and rotation.

The device may further include a rotatable element coupled to the distal tip, the rotatable element enabling the distal tip to at least rotate independently of the outer tube. The distal tip may be threaded. The engagement feature at the distal end of the cutting element and/or the mating feature at the proximal end of the distal tip may be configured to enable the distal tip to exhibit a hammer drill motion that comprises simultaneous rotation and repeated motions along the longitudinal axis. The cutting element may comprise one or more beaks configured to selectively assume open and closed configurations. One or more beaks may be configured to cycle through the open and closed configurations while rotating. The outer tube may comprise an outer cutting ribbon or threaded element configured to aid in tissue penetration.

According to one embodiment, a method of crossing a vascular occlusion may include providing a device comprising an outer tube defining a longitudinal axis and an aperture near a distal end thereof; a cutting element disposed within the outer tube, the cutting element comprising an engagement feature at a distal end thereof; and a distal tip comprising a tapered distal end and a proximal end comprising a mating feature. The method may further include introducing at least the distal tip into tissue; rotating and moving the cutting element within the outer tube along the longitudinal axis across the aperture to cut at least the vascular occlusion; advancing the cutting element until the engagement feature at the distal end thereof at least partially engages the mating feature at the proximal end of the distal tip and entrains the distal tip in rotation and oscillation along the longitudinal axis; and crossing the vascular occlusion while the cutting element cuts the vascular occlusion within the aperture and as the distal tip rotates and oscillates along the longitudinal axis. The method may further be carried out with the device further comprising a rotatable element coupled to the distal tip, the rotatable element enabling the distal tip to at least rotate independently of the outer tube. The distal tip may be threaded. The providing step may carried out with one or more of the engagement feature at the distal end of the cutting tip and the mating feature at the proximal end of the distal tip being configured to enable the distal tip to exhibit a hammer drill motion that comprises simultaneous rotation and repeated motions along the longitudinal axis. Providing may carried out with the cutting element comprising one or more beak configured to selectively assume open and closed configurations. The method may further comprise the one or more beaks cycling through the open and closed configurations while rotating. Providing may carried out with the outer tube comprising an outer cutting ribbon or threaded element configured to aid in tissue penetration.

According to one embodiment, a device for crossing a vascular occlusion may comprise an outer tube, the outer tube defining a longitudinal axis and comprising an aperture near a distal end thereof; a cutting element rotatably disposed within the outer tube and configured for movement along the longitudinal axis to cut vascular occlusive material within the aperture; and a distal tip, the distal tip being selectively configured to be at rest when not engaged by a distal end of the cutting element and to be entrained motion comprising oscillation along the longitudinal axis and/or rotation when engaged by the distal end of the cutting element.

The device may further comprise a rotatable element coupled to the distal tip, the rotatable element enabling the distal tip to at least rotate independently of the outer tube. The distal tip may threaded. The device may further comprise an engagement feature disposed at the distal end of the cutting tip; and a mating feature disposed at a proximal end of the distal tip, the engagement feature being configured to engage with the mating feature to entrain the distal tip in rotation and/or a hammer drill motion that comprises simultaneous rotation and repeated motions along the longitudinal axis. The cutting element may comprise one or more beaks configured to selectively assume open and closed configurations. The beak(s) may be configured to cycle through the open and closed configurations while rotating. The outer tube may comprise an outer cutting ribbon or threaded element configured to aid in tissue penetration.

DETAILED DESCRIPTION

Reference will now be made in detail to the construction and operation of embodiments illustrated in the accompanying drawings. The following description is only exemplary of the embodiments described and shown herein. The embodiments, therefore, are not limited to these implementations, but may be realized by other implementations.

According to one embodiment, a tissue biopsy forward coring and part off device, also referred to herein as an excisional device, may be configured to retrieve multiple samples of normal and/or abnormal appearing biological tissues or other materials during a single insertion through the skin (percutaneous procedure) into the, for example, soft or hard tissue area of the body from which the biopsy is taken. Embodiments may comprise structures and functionality for different phases of a multi-phase biopsy procedure, which may be performed by hand or with sufficient modification by attachment to a stereotactic table stage or Magnetic Resonance Imaging (MRI) stage. Embodiments of a biopsy device, along with associated related subcomponents described herein, may provide the capability to retrieve solid, contiguous and/or fragmented tissues as well as liquid and semi-solid tissues for analysis, diagnosis and treatment. Similar elements, structures, features and functionality contained in this disclosure are disclosed in co-pending and commonly assigned U.S. patent application Ser. No. 13/973, 898 entitled "SOFT TISSUE CORING BIOPSY DEVICES AND METHODS"; U.S. patent application Ser. No. 14/050, 771 entitled "SOFT TISSUE CORING BIOPSY DEVICES AND METHODS"; U.S. patent application Ser. No. 62/052, 070 entitled "SOFT TISSUE BIOPSY OR EXCISIONAL DEVICES AND METHODS"; U.S. patent application Ser. No. 62/052,591 entitled "IN-SITU MATERIAL DELIVERY DEVICES AND METHODS"; and U.S. patent application No. 61/876,977 entitled "TISSUE CORING BIOPSY DEVICES AND METHODS", the entire disclosures of which are hereby incorporated herein in their entirety.

Reference will now be made in detail to the construction and operation of embodiments illustrated in the accompanying drawings.

Figure 1:
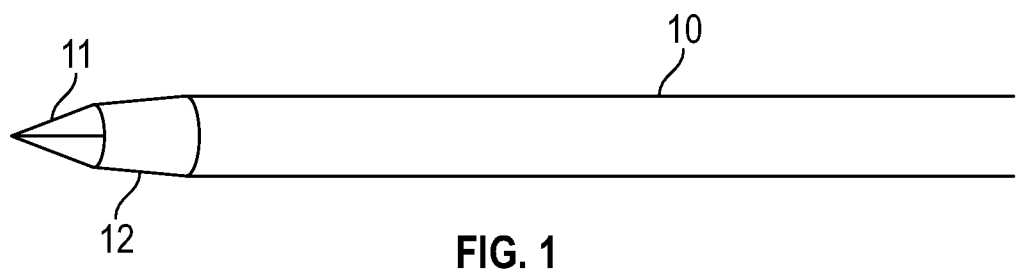
FIG. 1 is a side view of a tissue biopsy device, according to one embodiment.

FIG. 1 is a side view of the working end of a tissue biopsy device 10, according to one embodiment. In this view, a work element comprising a coring beak or beaks 11 is disposed at the distal end of a tissue biopsy tube set 10. In FIG. 1, the beaks 11 are shown in the closed position. These closed beaks 11 may be rotated and "jack hammered" as means to penetrate through tissues using principles of blunt dissection augmented by these additional actions. The tube set components of a biopsy device 10 are connected to other components of a biopsy instrument as described in detail below. Other components of biopsy device 10 may for example provide the mechanisms and actions including rotation, advancement and "jack hammering", which may also include rotational and axial oscillations of high frequency as well as including certain resonant frequencies of any range, so optimized to help break up certain hard tissues.

Figure 2:
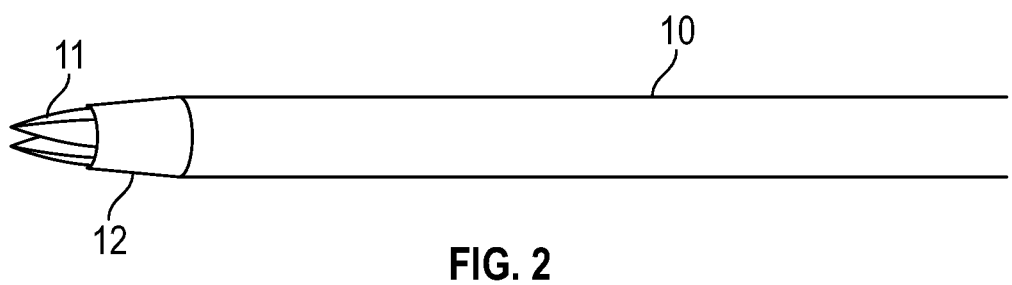
FIG. 2 is a side view of a tissue biopsy device, according to one embodiment.

FIG. 2 is a side view of the working end of the tissue biopsy device 10, according to one embodiment. In this view, a work element comprising a coring beak or beaks 11 may be disposed at the distal end of a tissue biopsy tube set 10. In FIG. 1, these beaks are shown in partially closed position. The beaks 11, which are illustrated partially closed (partially open) 11 may be rotated and "jack hammered" as well as infinitely cycled between various states of open and closed as a further means to penetrate through tissues, enabling modes of operation that are similar in concept to the way a surgeon uses various hand held instruments utilizing principles of blunt dissection combined with principles of sharp dissection. A biopsy instrument to which the working end is attached may provide many or all of these mechanisms and actions.

Figure 3:
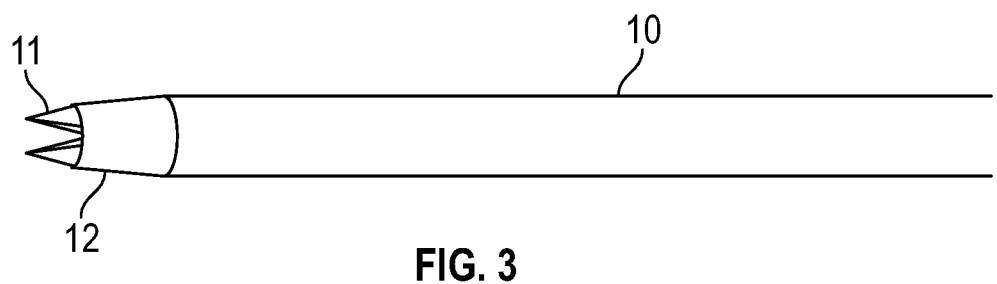
FIG. 3 is a side view of a tissue biopsy device, according to one embodiment.

FIG. 3 is a side view of the working end of a tissue biopsy device 10, according to one embodiment. In this view, a work element comprising a coring beak or beaks 11 may be disposed at the distal end of a tissue biopsy tube set 10. The beaks 11 are shown in wide open coring position in FIG. 3. These widely open beaks 11 may be rotated and "jack hammered" as means to penetrate through tissues and in the wide-open position, may collect tissues that enter the open end of the tube, using the beaks to part away a core of tissue sample. Once a desired position within the tissue is achieved or a sufficient tissue sample is cored, closing of the beaks 11 may serve to completely sever the cored tissue from its host organ or vessel. Such parting off may be accomplished by any or all of the actions listed for penetration function such as rotation, oscillation and others not limited to those listed including use alone or in combination, energized severing such as radiofrequency, ultrasonic, heat, cold and other forms of energy delivery. Element 12 is a tapered nose cone that may serve simply as a streamlining element and may also function as an opposite pole to beaks 11 in a bipolar radiofrequency electro-cautery surgical instrument system for example.

Figure 4:
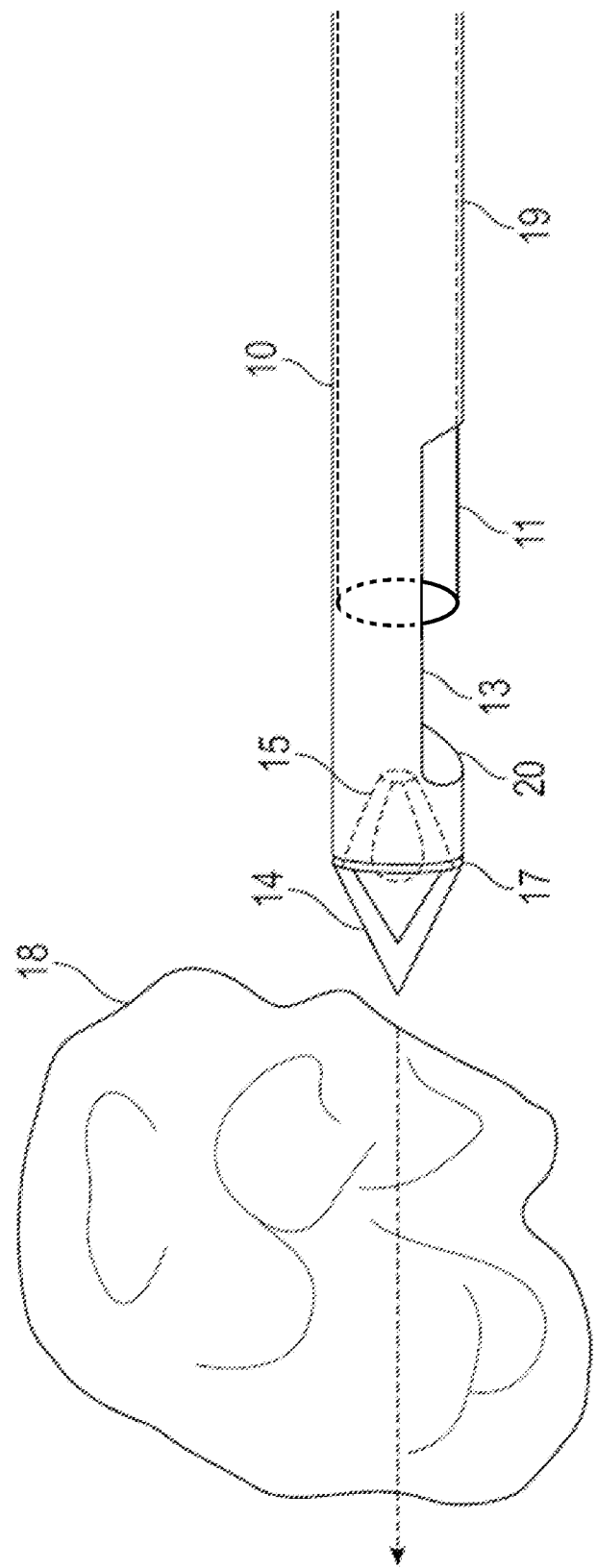
FIG. 4 is a side view of another tissue biopsy device, according to one embodiment.

FIG. 4 is a side view of assembled elements of a side aperture coring tube set of a tissue biopsy device, according to one embodiment. In this figure, it may be seen that the cutter element 11 is advanced through the non- or differentially rotating outer tube 19 and partially along the side aperture opening of chamber 13. Upon further advancement cutter 11 would first part-off a tissue specimen as it travels under the distal limit 20 of side aperture opening 13 and thereafter engage tapered wedge plunger 15. The engagement of for example, rotating cutter 11 with wedge element 15 would then cause tip 14 to also rotate to aid penetration through difficult to penetrate tissues. A rotatable element 17, configured to act like a turntable in this case, would permit tip 14 to rotate along with cutter 11, while outer tube 19 could remain still or differentially rotating to prevent or counter tissue windup.

Figure 5:
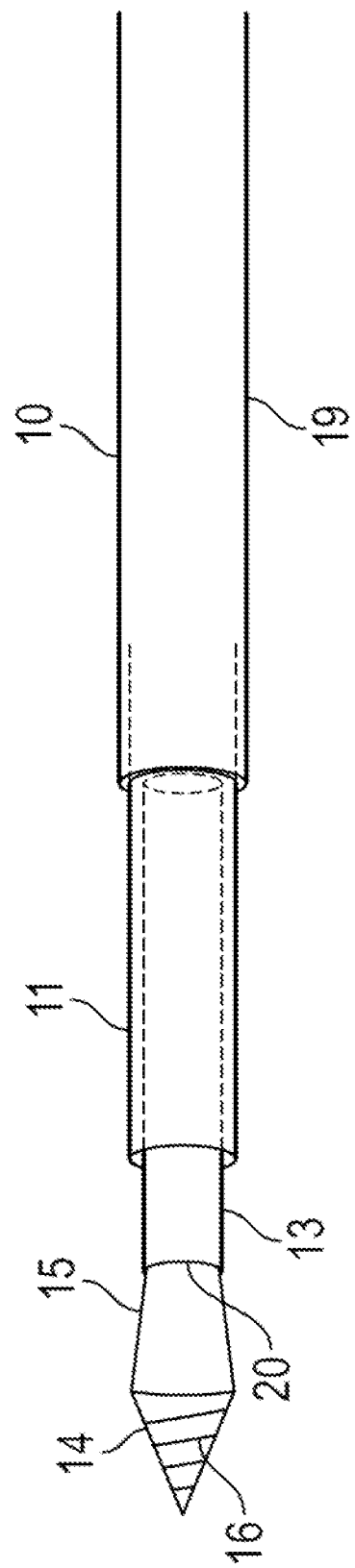
FIG. 5 is a side view of another tissue biopsy device, according to one embodiment.

FIG. 5 is a side view of assembled elements of a side aperture coring tube set of a tissue biopsy device, according to one embodiment. In this figure, it may be seen that the cutter element 11 is advanced through the non- or differentially rotating outer tube 19 and partially along the side aperture opening of chamber 13. Upon further advancement cutter 11 would first part-off a tissue specimen as it travels over wedge element 15 located near the distal limit 20 of side aperture opening 13 and thereafter engage tapered wedge plunger 15. The engagement of for example, rotating cutter 11 with wedge element 15 would then cause tip 14 to also rotate to aid penetration through difficult to penetrate tissues. In this embodiment, there is no need for a rotatable element 17, configured to act like a turntable since tip 14 may rotate along with cutter 11, while outer tube 19 could remain still or differentially rotating to prevent or counter tissue windup because outer tube 19 does not include chamber 13, which is disposed inside it. The distal tip 14 may be blunt or sharpened, and may include elements such as threads 16 to aid in forward advancement when rotating according to embodiments.

Figure 6:
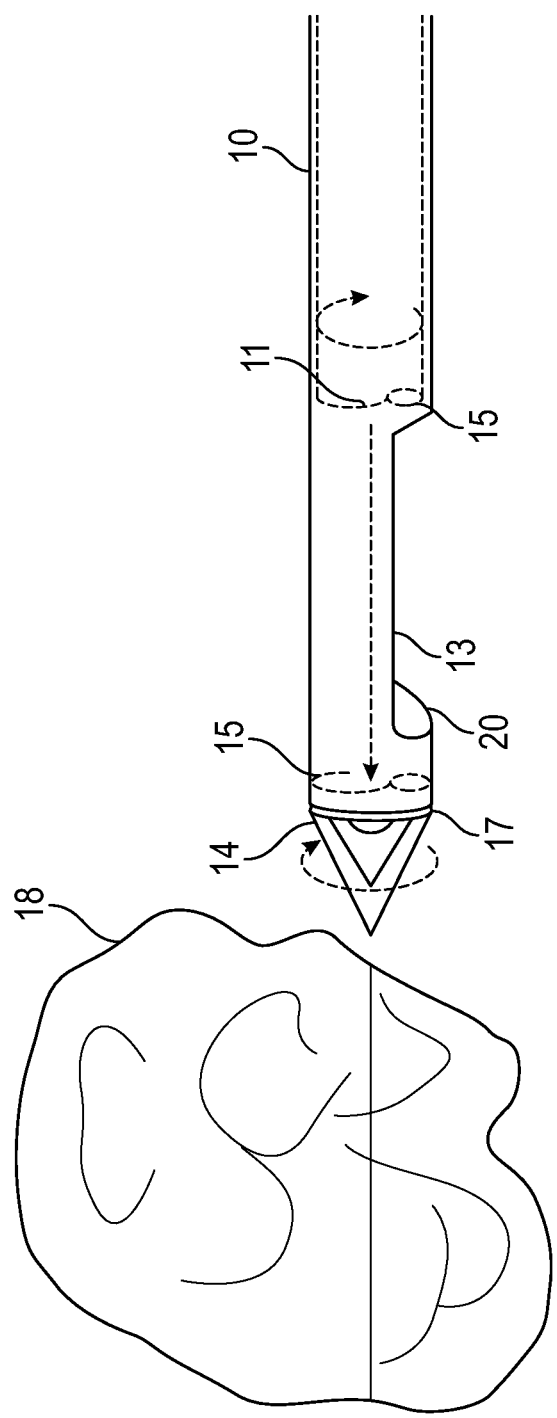
FIG. 6 is a side view of another tissue biopsy device, according to one embodiment.

FIG. 6 is a side view of assembled elements of a side aperture coring tube set of a tissue biopsy device, according to one embodiment. In this figure, it may be seen that the cutter element 11 is advanced through the non- or differentially rotating outer tube 19 and partially along the side aperture opening of chamber 13. Upon further advancement cutter 11 would first part-off a tissue specimen as it travels under the distal limit 20 of side aperture opening 13 and thereafter engage element 15 whose proximal face is shaped to engage for example, a similarly shaped sinusoidal cutter element 11. In the case where engagement is not sufficient to completely lock up and match rotational speeds of cutter 11, engagement shapes such as exemplified in this illustration would serve to create a "hammer drill" type of action on the tip 14, presuming that connection detail at element 17 includes freedom for some axial as well as rotational and oscillation motions to aid in penetration of difficult tissues. The complete lock-up engagement of for example, rotating cutter 11 with complementary matching element 15 would then cause tip 14 to also rotate at the same direction and speed as cutter 11 to aid penetration through difficult to penetrate tissues such as lesion 18. A rotatable element 17, configured to act like a turntable in this case with the possible addition of differential axial motion, would permit tip 14 additional motions as dictated by cutter 11, while outer tube 19 could remain as a stable non-moving or differentially moving component to prevent or counter unwanted host tissue reactions and all components of which may be of any desired dimension and according to embodiments.

Figure 7:
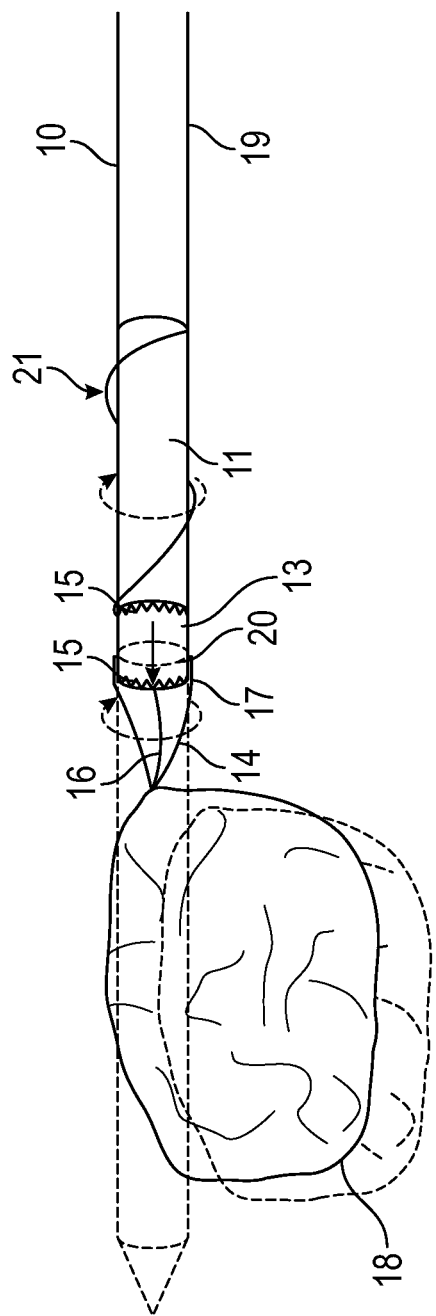
FIG. 7 is a side view of another tissue biopsy device, according to one embodiment.

FIG. 7 is a side view of assembled elements of a side aperture coring tube set of a tissue biopsy device, according to one embodiment. In this figure, it may be seen that the cutter element 11 is advanced through the non- or differentially rotating outer tube 19 and partially along the side aperture opening of chamber 13. Upon further advancement cutter 11 would first part-off a tissue specimen as it travels under the distal limit 20 of side aperture opening 13 and thereafter engage element 15 whose proximal edge is shaped to engage for example, a similarly shaped distal edge 15 cutter element 11. In the case where engagement is not sufficient to completely lock up and match rotational speeds of cutter 11, engagement shapes such as exemplified in this illustration would serve to create a "hammer drill" type of action on the tip 14, presuming that connection detail at element 17 includes freedom for some axial as well as rotational and oscillation motions to aid in penetration of difficult tissues. The complete lock-up engagement of for example, rotating cutter 11 with complementary matching element 15 would then cause tip 14 to also rotate at the same direction and speed as cutter 11 to aid penetration through difficult to penetrate tissues such as lesion 18. A rotatable element 17, configured to act like a turntable in this case with the possible addition of differential axial motion, would permit tip 14 additional motions as dictated by cutter 11. In this example, an additional feature such as an outer cutting ribbon or threaded element 21 is shown as a feature of cutter tube 11. A feature such as shown may further aid penetration by lowering resistance to travel of the portion of cutter tube 11 that is exposed to host tissue by virtue of its position beyond covering non- or differentially rotating outer tube 19, which again could remain as a stable non-moving or differentially moving component to prevent or counter unwanted host tissue reactions and all components of which may be of any desired dimension and according to methods.

One embodiment, therefore, is a device that incorporates principles of penetration through materials using alone or in combination, principles of powered blunt dissection, sharp dissection and energized dissection. Such a device may provide controlled activation of working coring beaks in a range of openings that enable a continuum of blunt, sharp and energized penetration and coring. One embodiment includes a tubular coring and part-off device whose coring and part-off functions include the ability to penetrate and core cyclically utilizing single or combined principles of blunt, sharp and energized dissection. The tubular coring and part-off device may comprise outer rotating surfaces that are configured to lower resistance of travel through tissues along the outer tubular surfaces of the tubular components. One embodiment is a device that comprises features on its tip or beak tips that provide traction by interacting with surrounding tissue to augment penetration through such tissues. The device may comprise a differentially rotating tip that provides a sharpened distal end that streamlines the distal end of the device during closed-beak tissue penetration. Such a device, according to one embodiment, provides rotational friction minimization during closed beak penetration. The device may comprise a differentially rotating outer tube that protects surrounding tissues from windup due to tip rotational motions. One embodiment of the device provides cyclical opening and closing of beaks during penetration to combine principles of blunt and sharp dissection. The device may be configured for energized dissection to its tip or beak-tips for severing tissue. The device may provide partial or complete motion matching of a cutter and a tip. One embodiment is a device that provides parting off of tissue by matching a self-sharpening cutter rim with a matching, tapered internal or external wedge. The device may be provided with oscillating, rotatable and/or energized beaks or tips that are separately controllable.

It is to be understood that the foregoing dimensions and any dimensions referred to herein are exemplary in nature only. Those of skill in this art will recognize that other dimensions and/or configurations may be implemented, depending upon the application, and that the elements of the device could be of any length or dimension, all of which are considered within the scope of this disclosure. Furthermore, any discussion of dimensions or ranges of dimensions or physical or dynamic aspects such as flow rates or ranges of motion or time factors outlined herein are exemplary in nature only and should not be considered to be limiting.

The entire device may be configured to be disposable or may be configured to be reusable in whole or in part. Embodiments of the present device may be modified to be electrically powered by one or more motors and batteries and/or external power sources through a simple electrical coupling to connect to an external power supply conveniently placed, for example, in the handle or proximal end of the present biopsy device. The entire device may also be internally or externally manually powered, mechanically powered or be powered by means such as compressed air, gas or pressurized fluid.

It is to be understood that the above descriptions are but exemplary methodologies and that one or more of the steps described above may be omitted, while other steps may be added thereto to any of these embodiments, depending on the target site within the body. Other operator method embodiments and device embodiments are supported as well. The order of some of the steps may additionally be changed, according to the desired procedure.

The present device may be formed of or comprise one or more biocompatible materials such as, for example, stainless steel or other biocompatible alloys, and may be made of, comprise or be coated with polymers, such as polyimide, and/or biopolymer materials as needed to optimize function(s). Some of the components may be purposely surface-treated differentially with respect to adjacent components, as detailed. The various gears or pulleys may be made of any suitable, commercially available materials such as nylons, polymers such as moldable plastics, and others. If used, the motor powering the various powered functions of the present biopsy device may be a commercially available electric DC motor. The handle of the present device may likewise be made of or comprise inexpensive, injection-molded plastic or other suitable rigid, easily hand held strong and lightweight material. The handle may be configured in such a way as to make it easily adaptable to one of any number of existing guiding platforms, such as stereotactic table stages. The materials used in the present biopsy device may also be carefully selected from a ferro-magnetic standpoint, such that the present biopsy device maintains compatibility with MRI equipment.

The power source may comprise an external commercially available AC to DC transformer approved for medical device use and plugged into the provided socket in the present biopsy device, or may comprise an enclosed battery of any suitable and commercially available power source. The battery may be of the one-time use disposable (and optionally recyclable) variety, or may be of the rechargeable variety. Additionally, other power sources, for example, mechanical linkages or compressed air motors, may be used.

While certain embodiments of the disclosure have been described, these embodiments have been presented by way of example only, and are not intended to limit the scope of the disclosure. Indeed, the novel methods, devices and systems described herein may be embodied in a variety of other forms and other applications. All such other applications making use of the principles disclosed herein for this device and that could be envisioned by one skilled in the art are therefore considered to be within the scope of this disclosure. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures and dimensions thereof may differ from those shown in the figures. Depending on the embodiment, certain steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A device, comprising:
    an outer tube defining a longitudinal axis and comprising an aperture near a distal end thereof;
    a cutting element disposed within the outer tube and configured for rotation and movement across the aperture along the longitudinal axis, the cutting element comprising an engagement feature at a distal end thereof; and
    a distal tip comprising a tapered distal end and a proximal end that comprises a mating feature, wherein the cutting element is configured to rotate and cut tissue as the cutting element moves along the longitudinal axis across the aperture until the engagement feature at least partially engages the mating feature of the proximal end of the distal tip and entrains the distal tip in at least one of oscillation along the longitudinal axis and rotation.

2. The device of claim 1, further comprising a rotatable element coupled to the distal tip, the rotatable element enabling the distal tip to at least rotate independently of the outer tube.

3. The device of claim 1, wherein the distal tip is threaded.

4. The device of claim 1, wherein at least one of the engagement feature at the distal end of the cutting element and the mating feature at the proximal end of the distal tip are configured to enable the distal tip to exhibit a hammer drill motion that comprises simultaneous rotation and repeated motions along the longitudinal axis.

5. The device of claim 1, wherein the cutting element comprises at least one beak configured to selectively assume open and closed configurations.

6. The device of claim 5, wherein the at least one beak is configured to cycle through the open and closed configurations while rotating.

7. The device of claim 1, wherein the outer tube comprises an outer cutting ribbon or threaded element configured to aid in tissue penetration.

8. A device for crossing a vascular occlusion, comprising:
    an outer tube, the outer tube defining a longitudinal axis and comprising an aperture near a distal end thereof;
    a cutting element rotatably disposed within the outer tube and configured for movement along the longitudinal axis to cut vascular occlusive material within the aperture; and
    a distal tip, the distal tip being selectively configured to be at rest when not engaged by a distal end of the cutting element and to be entrained in motion independently of the outer tube, the entrained motion comprising at least one of oscillation along the longitudinal axis and rotation when engaged by the distal end of the cutting element.

9. The device of claim 8, further comprising a rotatable element coupled to the distal tip, the rotatable element enabling the distal tip to at least rotate independently of the outer tube.

10. The device of claim 8, wherein the distal tip is threaded.

11. The device of claim 8, further comprising:
    an engagement feature disposed at the distal end of the cutting tip; and
    a mating feature disposed at a proximal end of the distal tip, the engagement feature being configured to engage with the mating feature to entrain the distal tip in at least one of rotation and a hammer drill motion that comprises simultaneous rotation and repeated motions along the longitudinal axis.

12. The device of claim 8, wherein the cutting element comprises at least one beak configured to selectively assume open and closed configurations.

13. The device of claim 12, wherein the at least one beak is configured to cycle through the open and closed configurations while rotating.

14. The device of claim 8, wherein the outer tube comprises an outer cutting ribbon or threaded element configured to aid in tissue penetration.

\* \* \* \* \*